United States Patent
Goddard, Jr.

(10) Patent No.: US 8,590,487 B1
(45) Date of Patent: Nov. 26, 2013

(54) ENCLOSURE FOR SMALL ANIMALS DURING AWAKE ANIMAL IMAGING

(71) Applicant: UT-Battelle, LLC, Oak Ridge, TN (US)

(72) Inventor: James S. Goddard, Jr., Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 13/676,460

(22) Filed: Nov. 14, 2012

(51) Int. Cl.
*A01K 29/00* (2006.01)

(52) U.S. Cl.
USPC .......................................... 119/417; 119/751

(58) Field of Classification Search
USPC .......... 119/417, 416, 421, 751, 752, 756, 755
See application file for complete search history.

(56) References Cited

U.S. PATENT DOCUMENTS

| | | | | | |
|---|---|---|---|---|---|
| 1,398,484 | A | * | 11/1921 | Holding | 119/752 |
| 2,540,650 | A | * | 2/1951 | Brosene, Jr. et al. | 119/751 |
| 3,739,751 | A | * | 6/1973 | Mohr et al. | 119/752 |
| 4,030,719 | A | * | 6/1977 | Gabriele et al. | 5/601 |
| 4,184,451 | A | * | 1/1980 | Carlin | 119/755 |
| 4,781,150 | A | * | 11/1988 | Phillips | 119/751 |
| 5,167,160 | A | * | 12/1992 | Hall, II | 73/864.91 |
| 5,320,069 | A | * | 6/1994 | Anderson et al. | 119/751 |
| 5,350,374 | A | * | 9/1994 | Smith | 606/5 |
| 5,927,234 | A | * | 7/1999 | Siegel | 119/751 |
| 6,651,587 | B1 | * | 11/2003 | DeFord et al. | 119/420 |
| 6,675,741 | B2 | * | 1/2004 | Remmler | 119/755 |
| 6,953,008 | B1 | * | 10/2005 | Remmler | 119/757 |
| 7,603,966 | B1 | * | 10/2009 | Beebe | 119/755 |
| 7,784,429 | B2 | * | 8/2010 | Chiodo | 119/417 |
| 7,992,523 | B1 | * | 8/2011 | Pugh | 119/751 |
| 8,170,302 | B1 | | 5/2012 | Gleason et al. | |
| 8,327,804 | B2 | * | 12/2012 | Yamada et al. | 119/421 |
| 2008/0317313 | A1 | | 12/2008 | Goddard et al. | |

* cited by examiner

*Primary Examiner* — Yvonne Abbott
(74) *Attorney, Agent, or Firm* — Colin L. Cini

(57) ABSTRACT

An enclosure or burrow restrains an awake animal during an imaging procedure. A tubular body, made from a radiolucent material that does not attenuate x-rays or gamma rays, accepts an awake animal. A proximal end of the body includes an attachment surface that corresponds to an attachment surface of an optically transparent and optically uniform window. An anti-reflective coating may be applied to an inner surface, an outer surface, or both surfaces of the window. Since the window is a separate element of the enclosure and it is not integrally formed as part of the body, it can be made with optically uniform thickness properties for improved motion tracking of markers on the animal with a camera during the imaging procedure. The motion tracking information is then used to compensate for animal movement in the image.

12 Claims, 5 Drawing Sheets

ENCLOSURE FOR SMALL ANIMALS DURING AWAKE ANIMAL IMAGING

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in the invention.

CROSS-REFERENCE TO RELATED APPLICATIONS

The present application relates to U.S. Pat. No. 8,170,302 "System and Method for Generating Motion Corrected Tomographic Images", and United States Patent Application Publication Number 2008/0317313 "System and Method for Tracking Motion for Generating Motion Corrected Tomographic Images", with each being incorporated herein by reference as if included at length.

THE NAMES OF THE PARTIES TO A JOINT RESEARCH AGREEMENT

None.

BACKGROUND OF THE INVENTION

1. Field of the Invention

The present disclosure relates to medical imaging of small animals and more specifically to an enclosure for accommodating small animals while being imaged in an awake state.

2. Description of the Related Art

Motion of a living subject during medical imaging procedures can cause image artifacts. The sources of motion can vary and may include restlessness, scratching, respiration and heart beating, to small movements due to pressure changes over the cardiac cycle. In some cases, motion artifacts degrade the diagnostic value of an image, wasting significant time and money.

Efficient methods for testing new drugs are very important to the pharmaceutical industry. The ability to screen test subjects for effects of a particular drug is an essential element in the process of product development. Small animals are essential for pharmaceutical testing, and mice, in particular, are useful for modeling human diseases. Efforts to scale down clinical medical imaging systems for smaller subjects have allowed medical researchers to obtain high-resolution computed tomography (CT) images of small animals for disease studies. Noninvasive imaging techniques, such as X-ray, CT, and positron emission tomography (PET), have been developed for small animal medical imaging applications. For example, small animal imaging is currently being used in cancer research to monitor tumor growth and regression in mice.

While anatomical models are useful for studying drug effectiveness, it is very often desirable to screen test subjects for physiological effects of a drug. PET and single photon emission computed tomography (SPECT) are among current techniques used for functional medical imaging. Because animal test subjects must be kept awake during the screening process in order to monitor functional processes, either the animal must remain motionless for the duration of the scan or its movements must be tracked, measured and recorded with a high degree of precision and accuracy. Unrestrained awake animals tend to move around rapidly and present imaging challenges. Although sedation and physical restraint can be used to impede animal motion for this type of medical scan, both methods have the potential to alter the neurological and physiological processes that are being studied.

U.S. Pat. No. 8,170,302 "System and Method for Generating Motion Corrected Tomographic Images", and United States Patent Application Publication Number 2008/0317313 "System and Method for Tracking Motion for Generating Motion Corrected Tomographic Images" both discuss the use of an enclosure or burrow to restrain an awake animal during imaging. Optical and reflective markers are adhered to the restrained but awake animal during imaging. Two or more cameras track the relative motion of the markers so that the animal's motion can later be accommodated for, and corrected, during image processing. The enclosure is optically transparent to the illumination wavelength and optically uniform so that the external images of the animal can be made without significant image distortion. A one-piece enclosure with optically uniform properties in the location of the optical and reflective markers can be challenging to manufacture.

Despite the teachings provided in the above publications, improvements to animal enclosures are needed in order to provide distortion-free images for motion tracking and further advance the art of small animal imaging for medical research.

BRIEF SUMMARY OF THE INVENTION

Disclosed are several examples of enclosures for restraining an animal during a medical imaging procedure. The enclosures include a tubular body made of a radiolucent material and a separate window made of an optically clear material that is affixed to the body. The window provides an undistorted view of the restrained animal during the medical imaging procedure. Because the window is a separate element of the enclosure, it can be made with optically uniform properties in the location of the reflective markers for improved motion tracking.

BRIEF DESCRIPTION OF THE SEVERAL VIEWS OF THE DRAWINGS

The apparatus may be better understood with reference to the following drawings and detailed description. Non-limiting and non-exhaustive descriptions are described with reference to the following drawings. The components in the figures are not necessarily to scale, emphasis instead being placed upon illustrating principles. In the drawings, like referenced numerals may refer to like parts throughout the different figures unless otherwise specified.

DETAILED DESCRIPTION OF THE INVENTION

Figure 1:
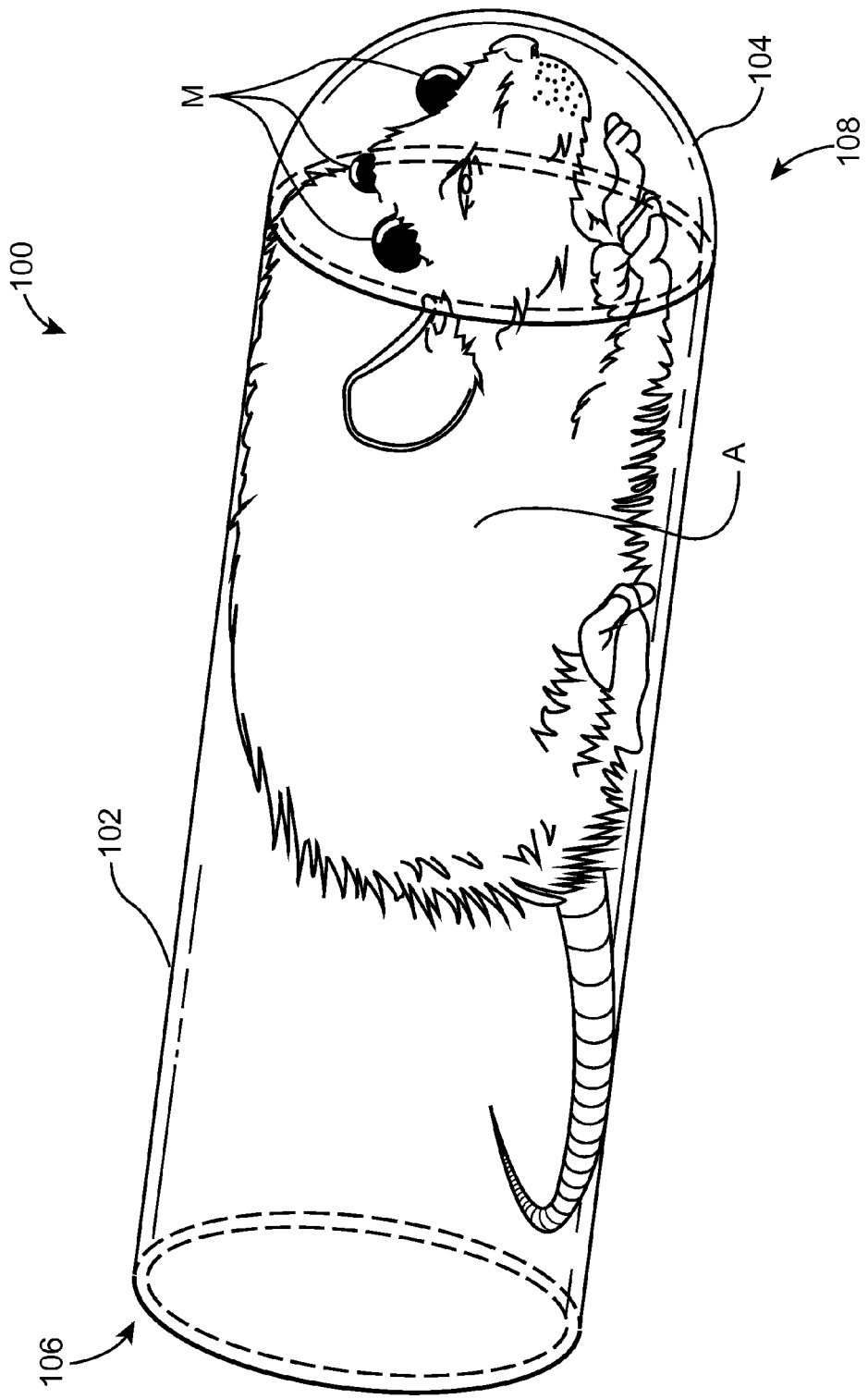
FIG. 1 illustrates an exemplary burrow with a restrained and animal.
Figure 2:
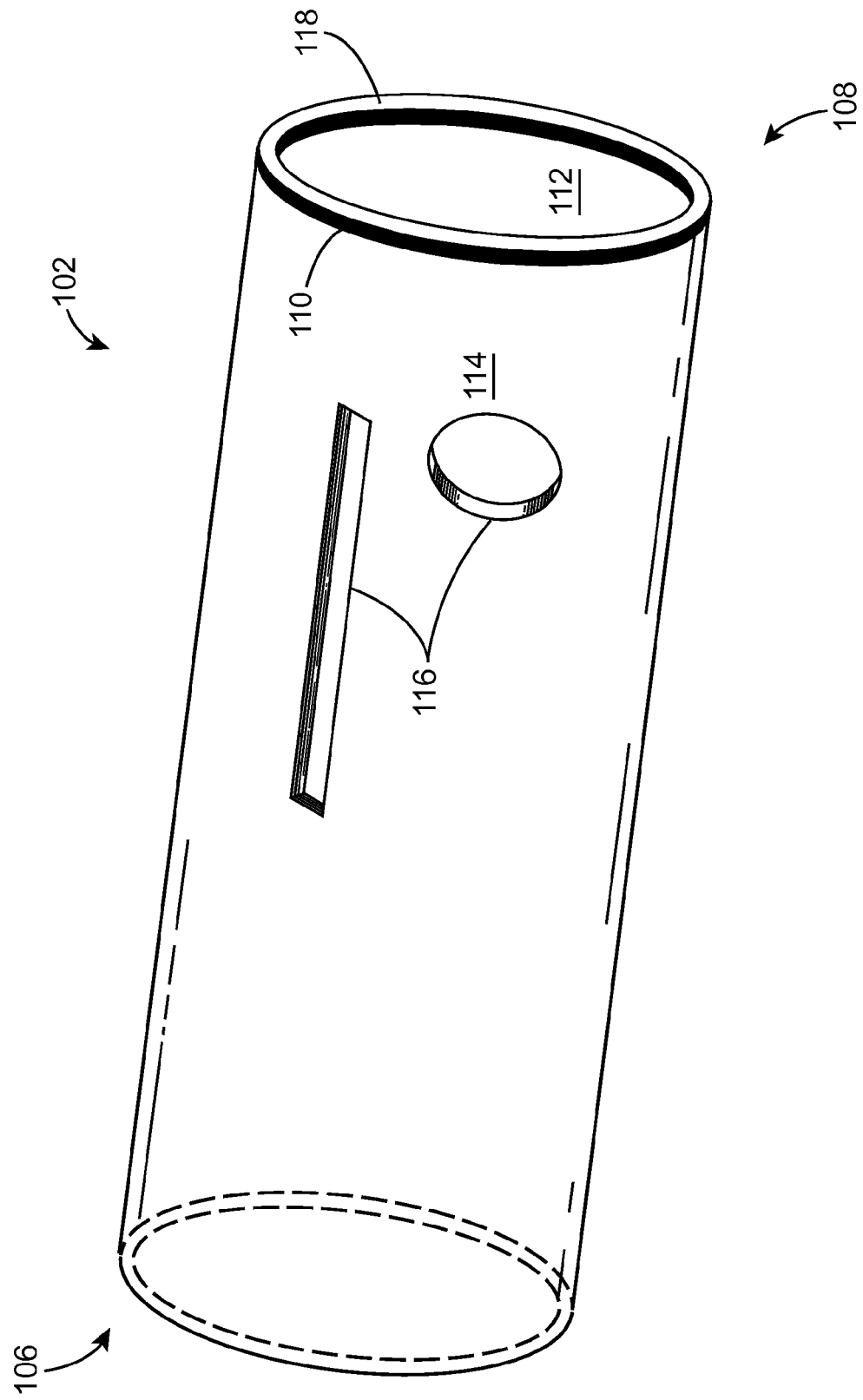
FIG. 2 illustrates an exemplary body portion of the burrow illustrated in FIG. 1.
Figure 3:
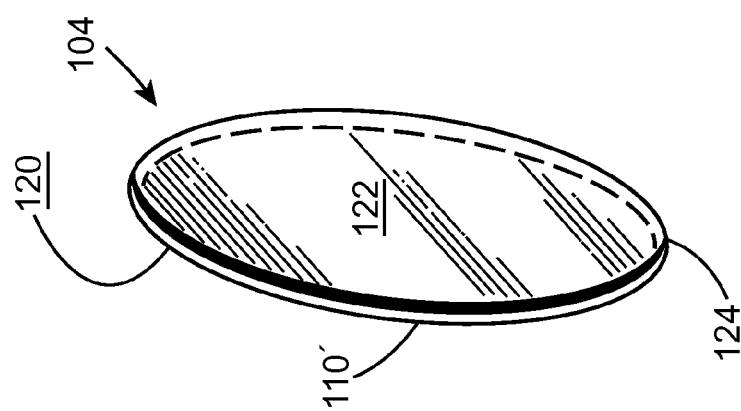
FIG. 3 illustrates exemplary window portions of the burrow illustrated in FIG. 1.
Figure 3:
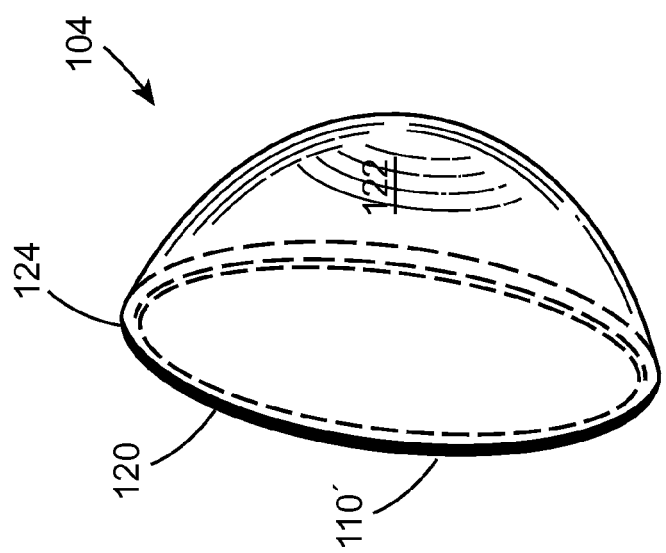
Figure 4:
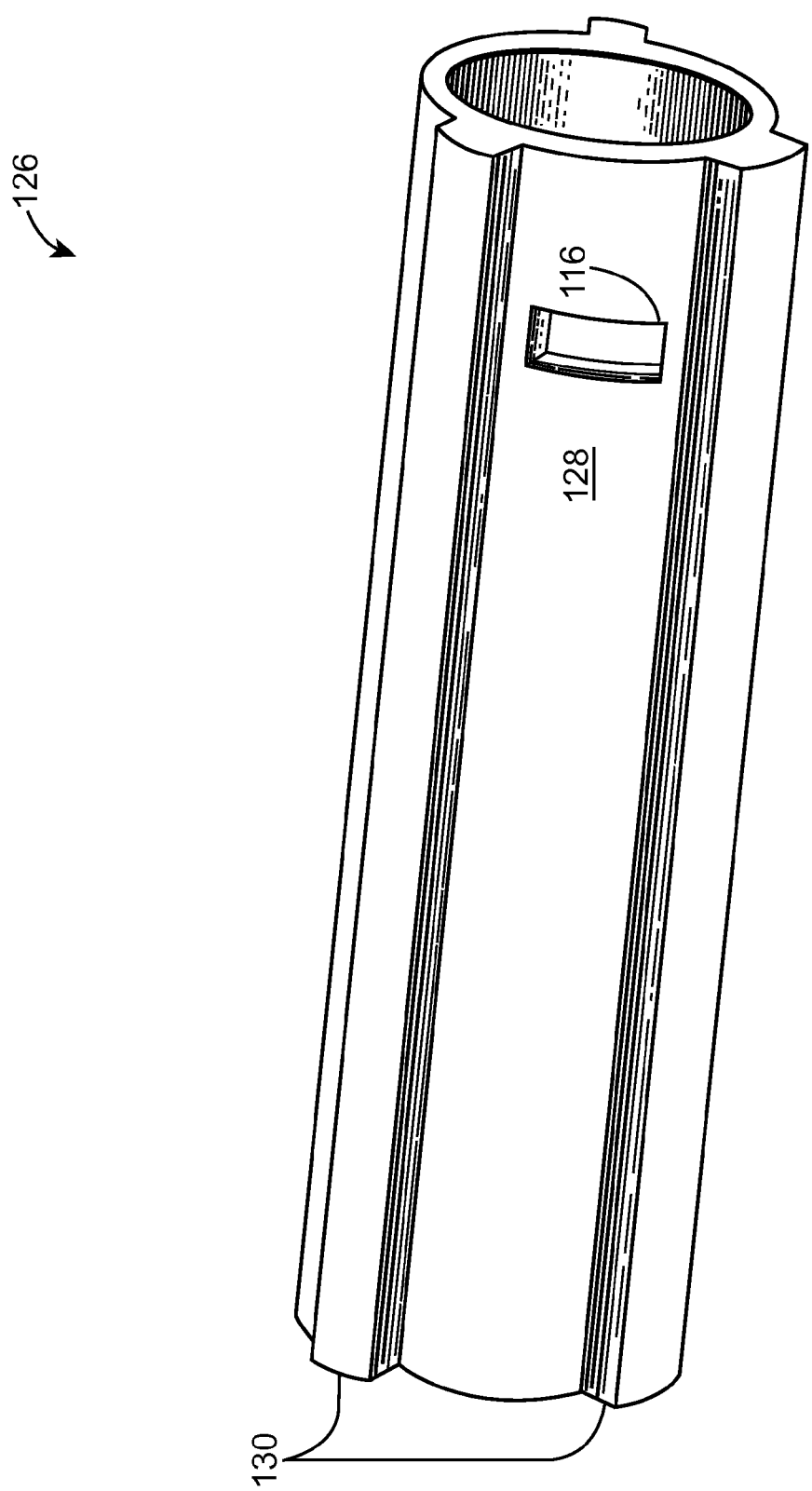
FIG. 4 illustrates an exemplary insert for use inside the body portion of FIG. 2.
Figure 5:
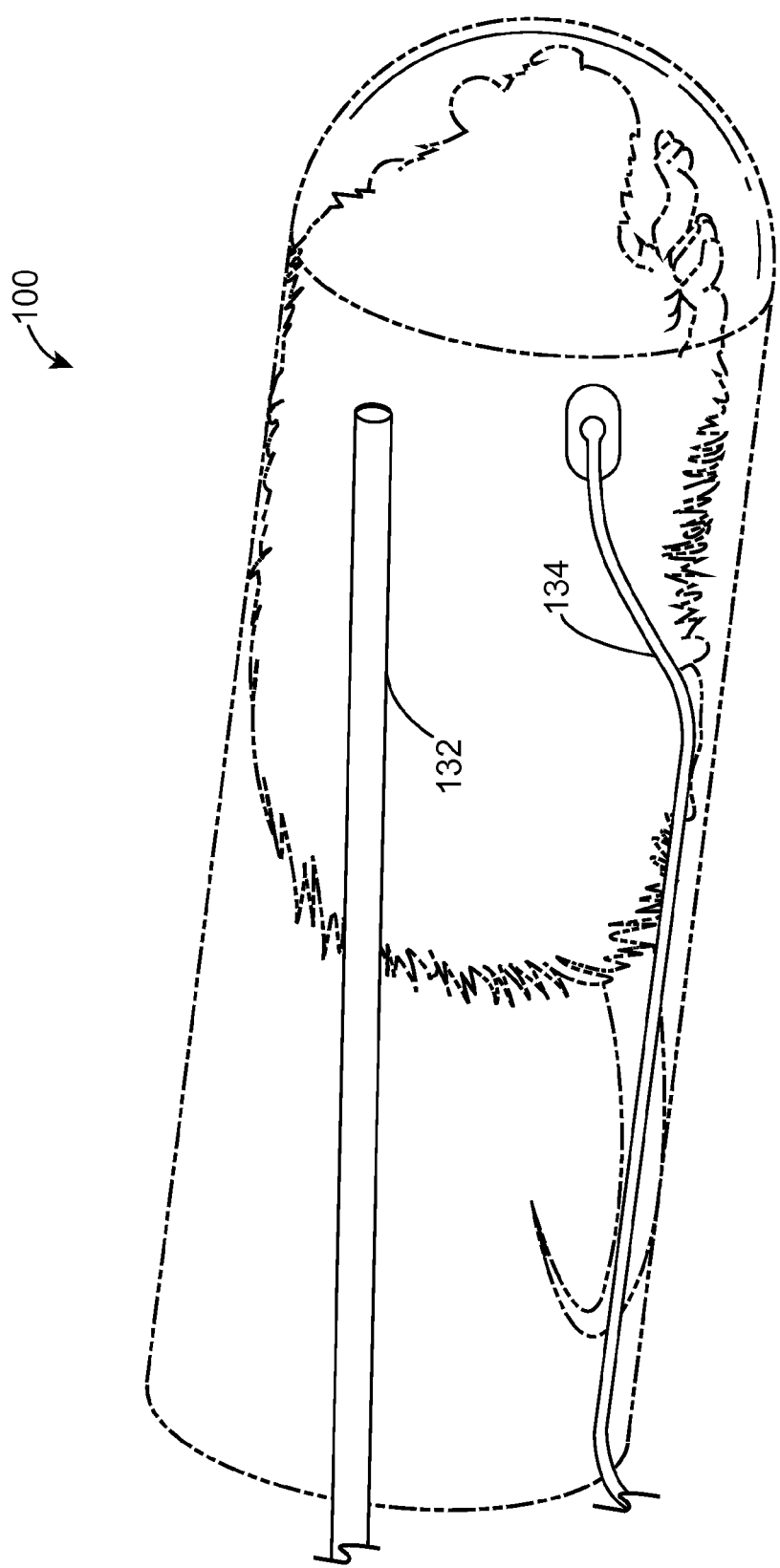
FIG. 5 illustrates an exemplary air supply means and sensing means for use with the burrow of FIG. 1.

Referring first to FIGS. 1-3, an enclosure 100 restrains an awake animal (A), such as a rat or a mouse, during a medical imaging procedure. In order to correct the images for the 3D motion of the awake animal (A), two cameras are used to capture the positions of the artificial markers (M) affixed to the animal (A), which are illuminated by infrared light emitting diodes (LEDs) as described in the incorporated references. The imaging procedure and motion correction equipment and methods are fully described in the incorporated references and a full description will not be included here for brevity. In the example of FIG. 1, the enclosure 100 includes a body 102 and a viewing window 104 that is a separate and detachable element from the body 102.

The body 102 is a tubular structure, defining an interior volume for accepting the animal (A), and having a cross sectional shape that is preferably circular (shown). Shapes such as square, rectangular, triangular, elliptical, or some other shape may be used. The shape of the body 102 must position and restrain the animal A to allow viewing of one or more optical markers (M), adhered to the animal (A), through the window 104 while the imaging procedure is being performed. A distal end 106 of the body 102 provides ingress and egress for the animal (A), while a proximal end 108 includes an attachment surface 110 for mating with a corresponding attachment surface 110' of the window 104.

Since the body 102 is disposed between the animal (A) and an imaging source (not shown), it must be made from a material that permits the passage of radiant energy with relatively little attenuation by absorption. Any radiolucent material that does not attenuate x-rays or gamma rays is suitable if it can be formed into the appropriate shape. Although optically clear PYREX brand glass tubes made by Corning Incorporated have been used successfully for the body 102, visible wavelength (optical) transparency is not required for this component. Glass can be formed into round tubular shapes with relative ease, but other shapes are possible as well.

Other radiolucent materials, such as, carbon fiber reinforced plastics, glass fiber reinforced plastics or Polyetheretherketon (PEEK) thermoplastic materials will allow radiant energy to pass through them with little attenuation. Since the body 102 does not require strong mechanical strength, a body 102 made from a plastic material is acceptable. A body 102 made from a plastic material is also relatively easy to form into numerous shapes and is inexpensive when compared with other materials. Depending on the material, injection molding, blow molding, spin molding, or other manufacturing processes may be used to form the body 102 into the required shape.

A diffuse or non-reflecting interior surface 112 of the body 102 is preferred in order to prevent specular reflections from being imaged by the optical motion cameras (not shown) through the window 104. The non-reflecting interior surface 112 may be a condition of the material selected, a surface treatment (e.g., sanded, sand blasted, etc. . . . ), or may be achieved with a coating as will be discussed in greater detail later. An opposite, exterior surface 114 faces away from the animal (A) and its reflectivity will not affect the optical motion cameras.

In some examples, the body 102 defines one or more apertures 116 for providing fresh air, food, medicine, or other items to the animal (A) during the imaging procedure. The apertures 116 may be circular, rectangular, slotted, or otherwise shaped and can be molded directly into the body 102 during forming, or can be machined into the body 102 after forming. The apertures 116 may be placed anywhere along the body 102, but placing one or more apertures 116 in close proximity to the animal (A) is preferred. The apertures also allow any water vapor to exit the enclosure 100 without forming condensation on the window 104.

The optically transparent and optically uniform window 104 is affixed to the proximal end 108 of the body 102 at cooperating attachment surfaces 110, 110' with an attachment means 118. The window 104 may be hemispherical dome shaped or may be flat disc shaped as shown in the examples of FIG. 3, or may be otherwise shaped. By manufacturing the window 104 as a separate component from the body 102, the optical clarity and uniformity of the thickness can be more closely controlled. A more uniform window 104 thickness improves the optical transparency, produces a very low optical distortion, and allows for more accurate motion tracking of the animal (A).

Optical glass such as BK7 glass available from ESCO Products provides excellent transmittance throughout the visible and near infrared spectra and down to 350 nm in the ultraviolet spectrum. A window thickness of up to 2 mm (0.079 inch) is preferred to avoid the need for optical correction, although windows of greater than 2 mm (0.079 inch) thickness may be used if the optical distortion is corrected. A thickness tolerance of +/−0.1 mm (0.004 inch) is generally sufficient to reduce optical distortion. Optics components are available from commercial vendors to meet the requirements for thickness, optical quality and thickness tolerance. Optical glass windows of 1 mm (0.039 inch) thickness have been used successfully for imaging of small animals (A).

The window 104 has both an interior surface 120 that faces the animal (A) and an opposite-facing exterior surface 122. In some examples, at least one of the interior 120 and exterior 122 surfaces is coated with an anti-reflective material 124. A coating of anti-reflective material 124 is optimized to allow the wavelength of light used to illuminate the animal (A) during the imaging procedure to pass through the window 104. This ensures that the infrared light emitting diodes don't produce reflections on the window 104 that would interfere with the 3D motion tracking.

Anti-reflective materials 124 reduce reflections due to illumination by means of optical interference. This reduction in reflections also increases the light transmission through the window 104, thus improving the contrast of the resulting image. Anti-reflective materials 124 are applied to the interior surfaces 120, the exterior surfaces 122, or both surfaces to achieve the bandwidth requirements and reflectance reduction. These include broadband and narrow bandpass coatings with single and multi-layers. Acceptable techniques for applying these coatings include evaporative and ion assisted deposition, advanced plasma reactive sputtering, and physical vapor deposition for example.

Both near-infrared and visible LED's are used for illumination of the markers (M) with wavelength ranges from 640 nm to 850 nm although wider wavelength ranges may be used as can other types of illumination. For these wavelengths, both broadband and narrowband anti-reflective coatings 124 can be used, although narrowband coatings will usually provide better anti-reflection results. Typically, maximum reflectivities of less than 1% are achieved with broadband coatings and less than 0.2% with narrowband coatings. Actual requirements for reflectivity depend on the specific application and the need to reduce artifacts (e.g., reflections) for image analysis. Parameters include wavelength, wavelength bandwidth, and angle of incidence with respect to reflection reduction. Anti-reflective materials such as Calcium Fluoride (CaF2) and various other metal oxides could also be used. An example of a low cost, anti-reflective material 124 is Magnesium Fluoride (MgF2) for broadband visible and near infrared applications. This material 124 can be applied using the physical vapor deposition process for example.

The equations that describe the total reflectance of a multi-layer film structure are given by:

$$\begin{bmatrix} B \\ C \end{bmatrix} = \left\{ \prod_{p=1}^{q} \begin{bmatrix} \cos\delta_p & i\sin\delta_p/\eta_p \\ i\eta_p\sin\delta_p & \cos\delta_p \end{bmatrix} \right\} \begin{bmatrix} 1 \\ \eta_\eta \end{bmatrix}$$

$$\delta_p = \frac{2\pi N_p d_p \cos\theta_p}{\lambda}$$

$$Y = \frac{C}{B}$$

$$R = \left(\frac{\eta_0 - Y}{\eta_0 + Y}\right)\left(\frac{\eta_0 - Y}{\eta_0 + Y}\right)$$

Where,
q: number of layers
δ: phase term
η: optical admittance of the layers
Np: Complex Refractive Index
tp: physical thickness of the layer
λ: wavelength
θp: angle of incidence
Y: the optical admittance of the stack
R: Reflectance of the stack The window 104 is affixed to the attachment surface 110 of the body 102 at a corresponding attachment surface 110' via attachment means 118. The corresponding attachment surfaces 110, 110' may have the same or different shapes and surface areas. In some examples, a silicone adhesive of the type offered by MasterBond of Hackensack, N.J., USA is used as the attachment means 118. The silicon adhesive remains pliant and allows the window 104 to be periodically removed from the body 102 for cleaning, coating, polishing, or replacement. In other examples, a snap fit, a threaded joint, hook and loop fasteners, magnets, or other means such as screws, clips, engaged pins or springs may be used as the attachment means 118.

In order to accommodate smaller sized animals (A) (e.g., juvenile mice) an insert 126 may be disposed inside the body 102 in some examples. The insert 126 decreases the volume of the body 102 to more adequately restrain the smaller sized animal (A) during an imaging procedure. The insert 126 includes a reducer portion 128 that defines a reduced volume for accepting the small animal (A). The reducer portion 128 may also define one or more apertures 116 as describe above with respect to the body 102. Two or more radially extending spacers 130 may extend from the reducer portion 128 and are appropriately sized to support and center the reducer portion 128 within the body 102. The reducer portion 128 preferably has a similar cross sectional shape as the body 102, but may have a different shape as well. The insert 126 is also made of a radiolucent material to allow imaging of the small animal (A) as described above with respect to the body 102.

In order to further prevent condensation from forming on the interior surface 120 of the window 104, an air supply means 132, such as a tube or a duct, may be disposed inside the body 102. A fan, pump, compressor, tank, or other air supply means (not shown) provides temperature and/or humidity controlled air to the animal (A) via the air supply means 132. Sensing means 134 may also be included within the body 102. The sensing means 134 may include sensors for monitoring one or more vital signs of the animal (A) such as heart rate, blood pressure, temperature for example.

While this disclosure describes and enables several examples of an enclosure for restraining awake animals, other examples and applications are contemplated. Accordingly, the invention is intended to embrace those alternatives, modifications, equivalents, and variations as fall within the broad scope of the appended claims. The technology disclosed and claimed herein may be available for licensing in specific fields of use by the assignee of record.

What is claimed is:

1. An enclosure for restraining an animal during a medical imaging procedure, the enclosure comprising:
   a tubular body made of a radiolucent material and forming a proximal end and a distal end;
   a window made of an optically transparent material affixed to said body at the proximal end, said window for providing an undistorted view of the restrained animal during the procedure so that one or more artificial markers affixed to the animal are viewable through said window for correcting the medical image for the motion of the animal; and
   wherein said window has a thickness of 2 mm (0.079 inch) or less and a uniformity of +/−0.1 mm (0.004 inch) or less.

2. The enclosure of claim 1 wherein said window is hemispherical dome shaped.

3. The enclosure of claim 1 wherein said window is flat disc shaped.

4. The enclosure of claim 1 wherein said window has an interior and an exterior surface and wherein at least one of the interior and exterior surfaces is coated with an anti-reflective material.

5. The enclosure of claim 4 wherein the anti-reflective material is magnesium fluoride (MgF2).

6. The enclosure of claim 1 wherein said window is affixed to said body with an adhesive material.

7. The enclosure of claim 1 wherein said body defines one or more apertures.

8. The enclosure of claim 7 wherein an aperture is circular shaped.

9. The enclosure of claim 7 wherein an aperture is slot shaped.

10. The enclosure of claim 1 and further comprising an insert disposed within said body for reducing the volume of said body.

11. The enclosure of claim 1 and further comprising an air supply means within said body.

12. The enclosure of claim 1 and further comprising animal sensing means within said body.

* * * * *

UNITED STATES PATENT AND TRADEMARK OFFICE
Certificate

Patent No. 8,590,487 B1                                                      Patented: November 26, 2013

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: James S. Goddard, Jr. Knoxvile, TN (US); and Justin S. Baba, Knoxville, TN (US).

Signed and Sealed this Twentieth Day of May 2014.

TIMOTHY D. COLLINS
*Supervisory Patent Examiner*
Art Unit 3644
Technology Center 3600